United States Patent [19]

Chupakhin et al.

[11] Patent Number: 6,028,068
[45] Date of Patent: Feb. 22, 2000

[54] SUBSTITUTED 6H-1,3,4-THIADIAZINE-2-AMINES, THE USE THEREOF AS ANAESTHETISING, CARDIOVASCULAR AND HYPOMETABOLIC AGENTS, AND A PHARMACEUTICAL COMPOSITION CONTAINING THEM

[75] Inventors: Oleg Nikolaevich Chupakhin; Larisa Petrovna Sidorova; Emma Afanasievna Tarakhty; Antonina Petrovna Novikova; Natalya Mikhailovna Perova, all of Ekaterinburg; Valentin Antonovich Vinogradov, Moscow, all of Russian Federation

[73] Assignees: The Procter & Gamble Company, Cincinnati, Ohio; Nauchno-Tekhnologicheskoe Predpriyatie "Ligand"(Tovarischestvo S Ogranichennoi Otvetstvennostju), Ekaterinburg, Russian Federation

[21] Appl. No.: 09/101,079
[22] PCT Filed: Dec. 28, 1995
[86] PCT No.: PCT/RU95/00286
    § 371 Date: Jan. 21, 1999
    § 102(e) Date: Jan. 21, 1999
[87] PCT Pub. No.: WO97/24353
    PCT Pub. Date: Jul. 10, 1997
[51] Int. Cl.⁷ .......................... C07D 285/16; A61K 31/54
[52] U.S. Cl. ......................... 514/222.5; 514/212; 544/8; 540/598
[58] Field of Search ............. 544/8; 514/222.5, 514/212; 540/598

[56] References Cited

U.S. PATENT DOCUMENTS

| | | | |
|---|---|---|---|
| 4,272,532 | 6/1981 | Jones et al. | 424/246 |
| 4,309,426 | 1/1982 | Jones, Jr. et al. | 424/246 |
| 4,558,045 | 12/1985 | Hargreaves et al. | 514/222 |
| 4,940,790 | 7/1990 | Thorwart et al. | 544/8 |
| 5,021,413 | 6/1991 | Terada et al. | 514/227.5 |
| 5,411,955 | 5/1995 | Strasser et al. | 514/214 |

FOREIGN PATENT DOCUMENTS

| | | |
|---|---|---|
| 884990 | 12/1980 | Belgium . |
| 884991 | 12/1980 | Belgium . |
| 2493844 | 5/1982 | France . |
| 220311 | 3/1985 | German Dem. Rep. . |
| 228248 | 10/1985 | German Dem. Rep. . |
| 3031703 | 3/1981 | Germany . |
| 3042295 | 6/1982 | Germany . |
| 49-88889 | 8/1974 | Japan . |
| 6253976 | 9/1994 | Japan . |
| 94007001 | 12/1995 | Russian Federation . |
| 1726478 | 4/1992 | U.S.S.R. . |
| 1827257 | 7/1993 | U.S.S.R. . |
| 2215206 | 9/1989 | United Kingdom . |
| 9322311 | 11/1993 | WIPO . |

OTHER PUBLICATIONS

Committee of the Russian Federation on Patents and Trade Marks Translation of RU 94007001 dated Dec. 20, 1995.

Osipova, N. A. "Evaluation of the Effect of Narcotic, Analgetic and Psychotropic Agents in Clinical Anesthesiology." The Meditsina Publishers, Leningrad (1988) Chapter 2, pp. 14–16 (English Translation of "Otsenka Effekta Narkoticheskikh, Analgeticheskikh I psikhotropnykh sredsto v klinicheskoi Anesteziologii." 1988, Meditsina, Leningrad, pp. 18–19).

Textbook of Anesthesiology, The Meditsina Publishers (1994) pp. 10–13 (English Translation of "Rukovodstvo po anesteziologii" pod redaktsiei Bunyatina A.A. (1994) Meditsina (Moscow) pp. 80–81).

"Side Effects of Drugs" Meditsina Publishers, Moscow (1983) pp. 1–6 (English Translation of "Pobochnye Deistvya Lekarstvennykh Sredstv" pod redaktsiei Djuska M.N.G. (1983) Meditsina, Moscow pp. 89–93).

The State Patent Office of the USSR (Gospatent of the USSR) English Translation of the Specification of SU 1827257 dated Jul. 15, 1993.

(List continued on next page.)

*Primary Examiner*—John M. Ford
*Attorney, Agent, or Firm*—Ladas & Parry

[57] ABSTRACT

Substituted 6H-1,3,4-thiadiazin-2-amines of the following general formula:

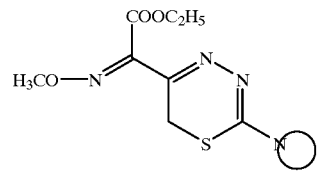

wherein

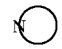

represents a morpholino, thiomorpholino, piperidino, pyrrolidino, or hexamethyienimino moiety, and pharmaceutically acceptable salts thereof which are used as anaesthetics, cardiovascular and hypometabolic agents, and the pharmaceutical compositions containing them.

8 Claims, No Drawings

OTHER PUBLICATIONS

Usoltseva S.V., et al. "1,3,4–Thiadiazines: Method of Synthesis and Reactivity." Khim. Geterotsikl. Soedin No. 4 (1991) pp. 435–448 And English comments thereon.

Novikova A.P., et al. "Synthesis and Properties of Functional Derivatives of 1,3,4. Thiadiazines . . . " Khim. Geterotsikl. Soedin No.: 11 (1991) pp. 1443–1457 And English comments thereon.

Rasina L.N., et al. "On Some Mechanisms of Action of Radioprotectors of Various Chemical Classes In Intestinal Syndrome" Radiobiologiya, 30(2) (1990) pp. 162–165 And English comments thereon.

Belik A.V. et al., "Prediction of A Class of Strong Toxicity of 1,3,4–Thiadiazine Derivatives" Khim–Farm. Zh., 26(3), (1992) pp. 62–64 And English comments thereon.

Perova N.M. et al., "Transformation of 2–Cycloalkylimino–6H–1–3–4–Thiadiazines under UV Irradiation" Khim. Geterotsikl. Soedin., No. 4, (1993) pp. 565–600 And English comments thereon.

Frasier et al. CA accession No. 1994:270462, 1994.

SUBSTITUTED 6H-1,3,4-THIADIAZINE-2-AMINES, THE USE THEREOF AS ANAESTHETISING, CARDIOVASCULAR AND HYPOMETABOLIC AGENTS, AND A PHARMACEUTICAL COMPOSITION CONTAINING THEM

This is a 371 of DCT/RU95/00286 filed Dec. 28, 1995.

TECHNICAL FIELD

This invention relates to novel 6H-1,3,4-thiadiazin-2-amine derivatives, to the use of them in medicine and veterinary as anaesthetics, cardiovascular and hypometabolic agents and to the pharmaceutical compositions containing them.

BACKGROUND OF THE INVENTION

Anaesthesia may generally be described as a state in which noxious events such as surgical procedures are rendered imperceptible by the body, the state being accompanied either by loss of consciousness (general anaesthesia) or no loss of consciousness (local anaesthesia). A complete or general anaesthetic given by inhalation or intravenous route produces a state of profound sleep and loss of motor activity (hypnosis), analgesia, muscle relaxation and protection against the increase in blood pressure and heart rate resulting from surgical stress. Anaesthetics generally display hypometabolic activity and frequently act as respiratory or cardiovascular depressants. Certain anaesthetics can be used to produce deliberate hypotensive effects which are very valuable in intracranial and other surgical procedures. Although a large number of agents having anaesthetic and cardiovascular activity have been identified and/or commercialised, there is a continuing need for new materials having hypometabolic activity, which are valuable for inducing sleep, reduction in motor activity, hypotension, bradycardiac, hypocoagulative, anti-aggregant and other hypobiosis effects such as reduced oxygen consumption and reduced body temperature, which would be valuable for use in complex surgical procedures or in the treatment of life threatening and/or traumatic situations such as brain stroke and myocardial infarction, and which have excellent potency, duration and CNS and cardiovascular toxicity profiles with absence of side effects such as tremor, convulsions and irregular breathing and heart beat.

There is considerable body of data concerning 6-R-1,3,4-thiadiazin-2-amines (for reviews see [1–3]). Also patent literature provides data on myo-relaxant [4–7], sedative [8,9], spasmolytic [10–12] and other types of biological activity [3]. A number of 5-aryl derivatives of 1,3,4-thiadiazines have been specifically described in the art [14–20] as well as 6-alkyl and 6-phenyl analogs thereof [13 and 21]. The value of 6-R-1,3,4-thiadiazin-2-amines as hypometabolic anaesthetic and cardiovascular agents has not hitherto been recognised however. Moreover, many of these compounds are apparently novel and have not been previously described in the literature.

The prior art on 6-R-1,3,4-thiadiazin-2-amines includes:
1. H. Beyer, Z. Chem., Bd. 9, S. 361, (1969).
2. S. V. Usoltseva, G. P. Andronnikova, and V. S. Mokrushin, Khim. Geterotsikl. Soedin., No 4, 435, (1991).
3. A. P. Novikova, N. M. Perova, and O. N. Chupakhin, Khim. Geterotsikl. Soedin., No 11, 1443, (1991)
4. W. D. Jones and F. P. Miller. U.S. Pat. No. 4,309,426 (1982).
5. W. D. Jones and F. P. Miller. BE-A-884,991 (1980).
6. W. D. Jones and F. P. Miller. DE-A-3,042,295 (1982).
7. FR-A-2,493,844 (1982).
8. U.S. Pat. No. 4,272,532 (1981).
9. F. P. Miller and W. D. Jones. BE-A-884,990 (1980).
10. W. D. Jones and F. P. Miller. DE-A-3,031,703 (1981).
11. Fisons PLC, Japan Kokai, Tokyo Koho JP-A-6253976.
12. W. D. Pfeiffer and E. Bulka, DD-A-220311 (1985).
13. N. Yoshida, K. Tanaka, and Y.Iizuka. Japan Kokai 7498889 (1974).
14. L. N. Rasina, 0. N. Chupakhin and M. V. Chibiryak. Radiobiologiya, 30(2), 162-5 (1990).
15. A. V. Belik et al, Khim.-Farm. Zh., 26(3), 62–64 (1992).
16. N. M. Perova et al, Khim. Geterotsikl. Soedin., No 4, 565–566 (1993).
17. E Bulka and W. D. Pfeiffer. DD-A-288824.
18. W. D. Pfeiffer and E Bulka, Synthesis, No 7, 485–6 (1977).
19. T Werner et al, U.S. Pat. No. 4,940,790 (1990).
20. A. P. Novikova et al, SU-A-1726478.
21. E Bulka et al, DD-A-228248.

SUMMARY OF THE INVENTION

According to one aspect of the invention, there is provided the use of substituted 6H-1,3,4-thiadiazin-2-amines of the following general formula as anaesthetic, cardiovascular and hypometabolic agents:

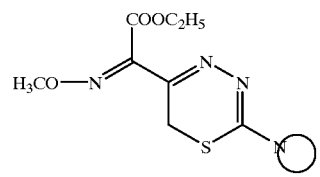

wherein

represents a morpholino, thiomorpholino, piperdino, pyrrolidino, or hexamethylenimino moiety; or pharmaceutically acceptable salts of said compounds.

According to a further aspect of the invention, there is provided novel substituted 6H-1,3,4-thiadiazin-2-amines of the general formula set out above.

According to a still further aspect of the invention, there is provided a pharmaceutical composition comprusing one or more of substituted 6H-1,3,4-thiadiazin-2-amines described above or pharmaceutically acceptable salts thereof.

DISCLOSURE OF THE INVENTION 1,3,4-Thiadiazines suitable for use herein are substituted at the 5 position of the thiadiazine ring with an ethoxalyl oxime moiety, they are presented by compounds in free form or by pharmaceutically-acceptable salts thereof. In addition, compounds are substituted at the 2 position of the thiadiazine ring with a cycloalkylimine moiety preferably selected from morpholino, thiomorpholino, piperidino and hexamethylenimino moieties.

The invention also relates to a process for the preparation of the 1,3,4-thiadiazines described above in which an ester (preferably ethyl ester) of γ-halo-α-methoxyiminoacetoacetic acid is reacted with a thiosemicarbazide of formula

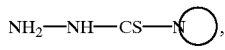

wherein

are as defined above.

The 1,3,4-thiadiazines can be isolated and/or used herein in free form or converted into additive salts with pharmacologically acceptable mineral or organic acids. Suitable for the preparation of acid addition salts are, for example, mineral acids, such as hydrobromic acid, hydrochloric acid, sulfuric acid or phosphoric acid; organic carboxylic acids, such as acetic. acid, lactic acid, maleic acid, fumaric acid, oxalic acid, tartaric acid, citric acid or gluconic acid; or organic sulfonic acids, such as benzenesulfonic acid, p-toluenesulfonic acid, methanesulfonic acid, trifluoromethansulfonic acid and cyclohexylamidosulfonic acid.

The substituted thiosemicarbazides which are employed as starting materials are generally known in the art or they may be prepared by the methods described in Houben-Weyl, Vol. E 4, pp. 506–515, and by K. A. Jensen et al., Acta Chem. Scand. 22 (1968), pp. 1–50. Thus, the thiosemicarbazides may be obtained by adding hydrazine to isothiocyanates or by reacting the appropriate N, N-di-substituted thiocarbamoyl chlorides with hydrazine or by reacting ethyl dithiocarbamates of formula

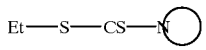

with hydrazine. In order to avoid interfering side reactions these preparations are advantageously carried out in aprotic solvents, such as, for example, chloroform, tetrachloromethane, diethyl ether or dioxan.

The reaction of γ-halo-α-methoxyaminoketoesters with thiosemicarbazide is expediently carried out using equimolar amounts of the both reagents in a solvent or diluent which is inert towards the reagents. Suitable for this purpose are, in particular, lower alcohols, such as methanol, ethanol, n-propanol, isopropanol, and the various butanols, or ethylacetate, and mixtures thereof, but ethanol is preferable. The reaction is generally carried out at temperatures in the range from about 5° C. to 30° C., preferably from about 18° C. to 20° C. Depending on the reactivity of the regents, the type of the reaction media and the reaction temperature used, reaction time may be between about 5 minutes and 2 hours. The final products are usually crystallized in analytically pure form on slow cooling of the reaction mixture.

Depending on their solubility the compounds may be administrated either by orally route or via parenteral injection in solution form. They may be administered either alone, for example in the form of microcapsules, and in mixtures with one another or in combination with suitable adjuvants and/or excipients.

Thus, the invention also relates to the pharmaceutical composition or medicament which comprises an effective amount of at least one of thiadiazine compounds as defined above, if appropriate, in the form of one of its acid addition salts, said composition comprises at least one of said active compounds in addition to pharmaceutically suitable excipients, diluents and/or other adjuvants. Suitable solid or liquid galenic formulations include, for example, granules, powders, coated tablets, tablets, (micro)capsules, suppositories, syrups, elixirs, suspensions, emulsions, drops, or injectable solutions, and also preparations having a protracted release of active compound, in the production of which adjuvants, such as excipients, disintegrants, binders, coating agents, swelling agents, glidants, lubricants, flavors, sweeteners or solubilizers are usually used. Suitable adjuvants include, for example, magnesium carbonate, titanium dioxide, lactose, mannitol and other sugars, talc, lactalbumin, gelatine, starch, cellulose and derivatives thereof, animal and vegetable oils, polyethylene glycols and solvents such ae sterile water and monohydric or polyhydric alcohols, for example glycerol.

The pharmaceutical preparations are preferably produced and administered in dosage units, each unit containing as active component a certain dose of at least one thiadiazine compound and/or at least one corresponding acid addition salt. In the case of injectable solutions the thiadiazine is preferably administered in dosages in the range from about 10 to about 600, preferably from about 20 to about 500, more preferably from about 30 to about 400 mg/kg.

Compounds suitable for use herein are represented by the following examples:

1. Ethyl-1-methoxyimino-1-(2-morpholino-6H-1,3,4-thiadiazine-5-yl)acetate, hydrobromide;
2. Ethyl-1-methoxyimino-1-(2-morpholino-6H-1,3,4-thiadiazine-5-yl)acetate, mesylate;
3. Ethyl-1-methoxyimino-1-(2-thiomorpholino-6H-1,3,4-thiadiazine-5-yl)acetate, hydrobromide;
4. Ethyl-1-methoxyimino-1-(2-thiomorpholino-6H-1,3,4-thiadiazine-5-yl)acetate, mesylate;
5. Ethyl-1-methoxyimino-1-(2-pyperidino-6H-1,3,4-thiadiazine-5-yl)acetate, hydrobromide;
6. Ethyl-1-methoxyimino-1-(2-pyrrolidino-6H-1,3,4-thiadiazine-5-yl)acetate, hydrobromide;
7. Ethyl-1-methoxyimino-1-(2-hexamethylenimino-6H-1,3,4-thiadiazine-5-yl)acetate, hydrobromide.

EXAMPLES

All compounds herein were obtained in 60–80% yields by condensation of ethyl γ-bromo-α-methoxyiminoacetoacetate with the corresponding 4-substituted thiosemicarbazides, proceeding smoothly on heating in ethanol. Evidence for the structure of the compounds is provided by their spectral ata (UV, IR, $^1$H NMR); their purity is confirmed by thin-layer chromatography and elemental analysis.

Example 1.

Ethyl-1-methoxyimino-1-(2-morpholino-6H-1,3,4-thiadiazine-5-yl)acetate, hydrobromide.

A cooled solution of 5 g (0.02 mole) of ethyl γ-bromo-α-methoxyaminoacetoacetate in 15 ml of absolute ethanol was added dropwise to a suspension of 3.2 g (0.02 mole) of morpholide of thiocarbazinic acid in 30 ml of absolute ethanol at 5–7° C. The mixture was stirred first at the above mentioned temperature for 2 h, and then at 18–20° C. for 5 h. Colorless precipitate was filtered off and crystallized twice from absolute ethanol. Yield 6.5 g (62%). M.p. 213–214° C. $R_f$=0.6 (eluent; butanol-acetic acid-water 4:1:5). Found, %: C, 36.7; H, 4.8; N, 14.3. $C_{12}H_{19}BrN_4O_4S$. Calculated, %: C, 36.5; H, 4.8; N, 14.2. $^1$H, NMR, DMSO-$d_6$, δ, ppm: 1.30 (3H, t, —$CH_3$, $COOC_2H_5$); 3.85 (8H, m, morpholino); 4.06 (2H, s, CH$_2$S); 4.10 (3H, s, OCH$_3$); 4.30 (2H, q, OCH$_2$—, COOC$_2$H$_5$).

Example 2.

Ethyl-1-methoxyimino-1-(2-morpholino-6H-1,3,4-thiadiazine-5-yl)acetate, mesylate.

Methanesulfonic acid, 0.7 g (0.007 mole), was added dropwise under stirring to a solution of 2 g (0.006 mole) of the compound 1 in dry benzene. A colorless precipitate obtained after 15–20 minutes of stirring, was filtered off and recrystallized from absolute ethanol. Yield 2.5 g (95%). M.p. 181–182° C. R$_f$=0.45 (eluent: butanol-acetic acid-water 4:1:5). Found, %: C, 38.2; H, 5.5; N, 13.6. C$_{13}$H$_{22}$N$_4$O$_7$S$_2$. Calculated, %: C, 38.1; H, 5.4; N, 13.7. $^1$H NMR, DMSO-d$_6$, δ, ppm: 1.28 (3H, t, —CH$_3$, COOC$_2$H$_5$); 2.35 (3H, c, SCH$_3$); 3.74 (8H, m, morpholino); 3.88 (2H, s, CH$_2$S); 4.02 (3H, s, OCH$_3$); 4.29 (2H, q, OCH$_2$—, COOC$_2$H$_5$).

Example 3.

Ethyl-1-methoxymiino-1-(2-thiomorpholino-6H-1,3,4-thiadiazine-5-yl)acetate, hydrobromide.

The compound 3 was prepared analogously to the synthesis of compound 1 by the reaction of ethyl γ-bromo-α-methoxyiminoacetoacetate with thiomorpholide of thiocarbazinic acid at 18–20° C. for 6 h. Yield 73%. M.p. 202–203° C. R$_f$=0.7(eluent; butanol-acetic acid-water 4:1;5). Found, %: C, 35.6; H, 4.8; N, 13.7. C$_{12}$H$_{19}$BrN$_4$O$_3$S$_2$. Calculated, %: C, 35.0; H, 4.6; N, 13.6. $^1$H NMR, DMSO-d$_6$, δ, ppm: 1.27 (3H, t, —CH$_3$, COOC$_2$H$_5$); 2.84 (4H, m, N(CH$_2$)$_2$, thiomorpholino); 4.06 (3H, s, OCH$_3$); 4.10 (4H, m, S(CH$_2$)$_2$, thiomorpholino); 4.17 (2H, s, CH$_2$S); 4.30 (2H, q, OCH$_2$—, COOC$_2$H$_5$).

Example 4.

Ethyl-1-methoxyimino-1-(2-thiomorpholino-6H-1,3,4-thiadiazine-5-yl)acetate, mesylate.

The compound 4 was prepared analogously to the synthesis of compound 2 from 2-thiomorpholino-5-ethoxalyl-6H-1,3,4-thiadiazine and methanesulfonic acid. Yield 90%. M.p. 171–172 ° C. R$_f$=0.59 (eluent: butanol-acetic acid-water 4:1:5). Found %: C, 36.4; H, 5.4; N, 13.2. C$_{13}$H$_{22}$N$_4$O$_6$S$_3$. Calculated, %: C, 36.6; H, 5.2; N, 13.1. $^1$H NMR, DMSO-d$_6$, δ, ppm: 1.34(3H, s, —CH$_3$); 2.33 (3H, s, SCH$_3$); 2.9 [4H, m, N(CH$_2$)$_2$, thiomorpholino]; 3.90 (3H, s, OCH$_3$); 4.10 [4H, m, S(CH$_2$)$_2$, thiomorpholino]; 4.18 (2H, s, CH$_2$S); 4.32 (2H, q, OCH$_2$—, COOC$_2$H$_5$).

Example 5.

Ethyl-1-metboxyimino-1-(2-pyperidino-6H-1,3,4-thiadiazine-5-yl)acetate, hydrobromide.

The compound 5 was prepared eialogously to the synthesis of compound 1 from ethyl γ-bromo-α-methoxyiminoacetoacetate and 4,4-pentamethylenthiosemicarbazide. Yield 67%. M.p. 201–202° C. R$_f$=0.35 (eluent: butanol-acetic acid water 4:1:5). Found, %: C, 39.5; H, 5.3; N, 14.3. C$_{13}$H$_{21}$BrN$_4$O$_3$S. Calculated, %: C, 39.7; H, 5.3; N, 14.3. $^1$H NMR, DMSO-d$_6$, δ, ppm: 1.32 (3H, t, —CH$_3$, COOC$_2$H$_5$); 1.72 (6H, m, piperidino); 3.68 (4H, m, piperidino); 4.08 (2H, s, CH$_2$S); 4.10 (3H, s, OCH$_3$); 4.32 (2H, q, OCH$_2$—, COOC$_2$H$_5$).

Example 6.

Ethyl-1-methoxyimino-1-(2-pyrrolidino-6H-1,3,4-thiadiazine-5-yl)acetate, hydrobromide;

The compound 6 was prepared analogously to the synthesis of compound 1 from ethyl γ-bromo-α-methoxyiminoacetoacetate and 4,4-tetramethylenthiosemicarbazide. Yield 59%. M.p. 208–209° C. R$_f$=0.29 (eluent: butanol-acetic acid-water 4:1:5). Found, %: C, 38.0; H, 5.1; N, 15.0. C$_{12}$H$_{19}$BrN$_4$O$_3$S. Calculated, %: C, 38.0; H, 5.0; N 14.8. $^1$H NMR, DMSO-d$_6$, δ, ppm: 1.31 (3H, t, —CH$_3$, COOC$_2$H$_5$); 1.90–2.03 (4H, m, pyrrolidino); 3.50–3.95 (4H, m, pyrrolidino); 4.06 (2H, s, CH$_2$S); 4.17 (3H, c, OCH$_3$); 4.32 (2H, q, OCH$_2$—, COOC$_2$H$_5$)

Example 7.

Ethyl-1-methoxyimino-1-(2-hexamethylenimino-6H-1,3,4-thiadiazine-5-yl)acetate, hydrobromide.

The compound 7 was prepared analogously to the synthesis of compound 1 from ethyl γ-bromo-α-methoxyiminoacetoacetate and 4,4-hexamethylenthiosemicarbazide. Yield 60%. M.p. 186 187° C. R$_f$=0.3 (eluent; butanol-acetic acid-water 4;1:5). Found, %: C, 41.8; H, 5.2; N, 13.5. C$_{14}$H$_{23}$BrN$_4$O$_3$S. Calculated, %: C, 41.3; H, 5.7; N 13.5. $^1$H NMR, DMSO-d$_6$, δ, ppm: 1.30 (3H, t, —CH$_3$, COOC$_2$H$_5$); 1.5–2.1 (8H, m, hexamethylenimino); 3.75–4.0 (4H, m, hexamethylenimino); 4.05 (2H, s, CH$_2$S); 4.18 (3H, s, OCH$_3$); 4.35 (2H, q, OCH$_2$—, COOC$_2$H$_5$).

EXPERIMENTAL BIOLOGICAL PART

The hypometabolic activity of the compounds according to the invention was demonstrated as follows. In all cases trials were carried out on mice of the BALB line of 3–4 month age. Non-toxic doses of compounds under test, varying from 60 to 400 mg/kg, were used in all experiments. In the case of water-soluble compounds aqueous solutions of the test compounds were injected intraperitoneally (i.p.), while water-insoluble compounds were introduced orally (p.o.).

In order to demonstrate the effect of the compounds herein on body temperature and oxygen consumption, in-vivo experiments were run using 5–6 mice per dosage.

Rectal temperature changes (absolute magnitudes in ° C.) were measured using a medicinal electrothermometer TREM-1 (Table 1). The rate of oxygen consumption was monitored by measuring concentration of oxygen in a closed testing unit with optic-acoustic gas analyzer MN 5130. The data on oxygen consumption are given an percents relative to the starting content of oxygen taken as 100 (Table 2).

When used in non-toxic doses all compounds were found to decrease rectal temperature in the range from 3 to 15° C. depending on the structure, dosage and method of introduction. It has been established that some of the tested compounds show sharp drop in body temperature (7–8° C. per 30 minutes), while others demonstrate only moderate effect (7–10° C. per 3 hours), as illustrated in Table 1.

Compound 1 was dissolved in a twin-water 1:9 (concentration of saturated solution was 40 mg/ml) and introduced intraperitoneally at the rate of 0.2 ml per 20 g of mouse weight. LD$_{16}$, LD$_{50}$, LD$_{84}$ were determined to be 788.4; 830.5, and 881.5 mg/kg. Introduction of the compound 1 caused drop of body temperature, akiriesia, suppression of reflexes to external disturbance, lateral state of mice.

Data on oxygen consumption over 10–300 minutes at 30 minute intervals are presented in Table 2. It was found that compound 1 lowers consumption of oxygen 7–10 fold during the first hour, 3–4 fold for the next 2 hours, and 2 fold at the fourth hour relative the initial value (Table 2).

Rectal temperature of mice and rats fell 10 minutes introduction by about 3–4° C. and after 30 minutes by about 7–8° C. for mice and about 5° C. for rats. The maximum temperature drop (12–13° C.) was reached in 90–120 minutes for mice and after five hours, the temperature difference was 2° C. Full restoration of oxygen consumption was not observed (Table 2).

TABLE 1

Effects of 1,3,4-thiadiazines on body temperature in experiments on mice

| Compound | Dose mg/kg (mM/kg) | Administration | Time of measurements in minutes | | | |
|---|---|---|---|---|---|---|
| | | | 0 | 30 | 60 | 90 |
| 1 | 391.7(1.0) | i.p. | 37.9 | 29.6 | 26.5 | 24.8 |
| 2 | 410.0(1.0) | i.p. | 38.5 | 31.9 | 32.8 | 35.3 |
| 4 | 166.0(0.39) | i.p. | 38.1 | 33.9 | 34.9 | — |

| Compound | Dose mg/kg (mM/kg) | Administration | Time of measurements in minutes | | | |
|---|---|---|---|---|---|---|
| | | | 120 | 180 | 240 | 300 |
| 1 | 391.7(1.0) | i.p. | 24.6 | 32.6 | 34.6 | 35.9 |
| 2 | 410.0(1.0) | i.p. | 36.4 | 37.6 | 38.8 | — |
| 4 | 166.0(0.39) | i.p. | 35.7 | 37.4 | — | — |

TABLE 2

Effects of Compound 1 on body temperature (T) and consumption of oxygen ($O_2$) in experiments on mice

| Compound | Dose (½LD$_{16}$) mg/kg (mM/kg) | Index | Time in measurements in minutes | | | | |
|---|---|---|---|---|---|---|---|
| | | | 0 | 5 | 15 | 30 | 60 |
| 1 | 390(1.0) | T | 37.9 | 33.5 | 31.2 | 29.6 | 26.5 |
| | | $O_2$ | ±0.1 | ±0.1 | ±0.1 | ±0.2 | ±0.1 |
| | | | 100 | 8.1 | 0.1 | 0.2 | 12.0 |

| Compound | Dose (½LD$_{16}$) mg/kg (mM/kg) | Index | Time in measurements in minutes | | | | |
|---|---|---|---|---|---|---|---|
| | | | 90 | 120 | 180 | 240 | 300 |
| 1 | 390(1.0) | T | 24.8 | 24.6 | 32.6 | 34.6 | 35.9 |
| | | $O_2$ | ±0.1 | ±0.1 | ±0.1 | ±0.2 | ±0.2 |
| | | | 27.0 | 26.0 | 28.0 | 59.0 | — |

We claim:

1. Substituted 6H-1,3,4-thiadiazin-2-amines of the general formula

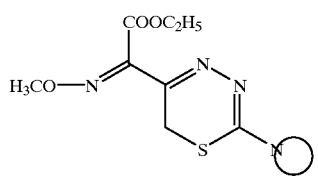

wherein

represents a morpholino, thiomorpholino, piperidino, pyrrolidino, or hexamethylenimino moiety; and pharmaceutically acceptable salts thereof.

2. Substituted 6H-1,3,4-thiadiazin-2-amines according to claim 1 selected from following group:

ethyl-1-methoxyimino-1-(2-morpholino-6H-1,3,4-thiadiazine-5-yl)acetate;

ethyl-1-methoxyimino-1-(2-thiomorpholino-6H-1,3,4-thiadiazine-5-yl)acetate;

ethyl-1-methoxyimino-1-(2-pyperidino-6H-1,3,4-thiadiazine-5-yl)acetate;

ethyl-1-methoxyimino-1-(2-pyrrolidino-6H-1,3,4-thiadiazine-5-yl)acetate;

ethyl-1-methoxyimino-1 (2-hexamethylenimino-6H-1,3,4-thiadiazine-5-yl)acetate; and the pharmaceutically acceptable salts thereof.

3. A method of inducing anaesthesia which comprises administering to a patient an anesthetically effective does of a compound selected from substituted 6H-1,3,4-thiadiazin-2-amines having the following formula:

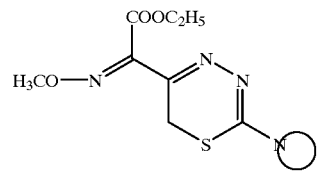

wherein

represents a morpholino, thiomorpholino, piperidino, pyrrolidino, or hexamethylenimino moiety.

4. A method according to claim 3, wherein the substituted 6H-1,3,4-thiadiazin-2-amine is selected from the following group:

ethyl-1-methoxyimino-1-(2-morpholino-6H-1,3,4-thiadiazine-5-yl)acetate, ethyl-1-methoxyimino-1-(2-thiomorpholino-6H-1,3,4-thiadiazine-5-yl)acetate, ethyl-1-methoxyimino-1-(2-pyperidino-6H-1,3,4-thiadiazine-5-yl)acetate, ethyl-1-methoxyimino-1-(2-pyrrolidino-6H-1,3,4-thiadiazine-5-yl)acetate, ethyl-1-methoxyimino-1-(2-hexamethylenimino-6H-1,3, 4-thiadiazine-5-yl)acetate, and pharmaceutically acceptable salts thereof.

5. A pharmaceutical composition comprising an effective amount of an active ingredient and pharmaceutically suitable excipient, diluent and/or other adjuvants, characterized in that said composition comprises as an active ingredient at least one of the compound of the formula:

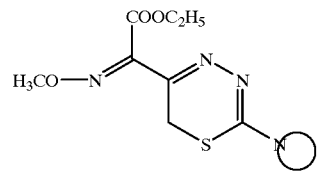

wherein

represents a morpholino, thiomorpholino, piperidino, pyrrolidino, or hexamethylenimino moiety; or pharmaceutically acceptable salt thereof.

6. A pharmaceutical composition according to claim 5 characterized in that it comprises as an active ingredient substituted 6H-1,3,4-thiadiazin-2-amine selected from the following group:

ethyl-1-methoxyimino-1-(2-morpholino-6H-1,3,4-thiadiazine-5-yl)acetate, ethyl-1-methoxyimino-1-(2-thiomorpholino-6H-1,3,4-thiadiazine-5-yl)acetate, ethyl-1-methoxyimino-1-(2-thiomorpholino-6H-1,3,4-thiadiazine-5-yl)acetate, ethyl-1-methoxyimino-1-(2-pyperidino-6H-1,3,4-thiadiazine-5-yl)acetate, ethyl-1-methoxyimino-1-(2-pyrrolidino-6H-1,3,4-thiadiazine-5-yl)acetate, ethyl-1-methoxyimino-1-(2-hexamethylenimino-6H-1,3,4-thiadiazine-5-yl)acetate, and pharmaceutically acceptable salts thereof.

7. A method of treating a cardiovascular or hypometabolic condition which comprises administering to a patient suffering from such a condition a therapeutically effective amount of a substituted 6H-1,3,4-thiadiazin-2-amine having the following formula:

wherein represents a morpholino, thiomorpholino, piperidino, pyrrolidino, or hexamethylenimino moiety.

8. A method according to claim 7, wherein the substituted 6H-1,3,4-thiadiazin-2-amine is selected from the following group:

ethyl-1-methoxyimino-1-(2-morpholino-6H-1,3,4-thiadiazine-5-yl)acetate, ethyl-1-methoxyimino-1-(2-thiomorpholino-6H-1,3,4-thiadiazine-5-yl)acetate, ethyl-1-methoxyimino-1-(2-pyperidino-6H-1,3,4-thiadiazine-5-yl)acetate, ethyl-1-methoxyimino-1-(2-pyrrolidino-6H-1,3,4-thiadiazine-5-yl)acetate, ethyl-1-methoxyimino-1-(2-hexamethylenimino-6H-1,3,4-thiadiazine-5-yl)acetate, and pharmaceutically acceptable salts thereof.

* * * * *